United States Patent
Reedy et al.

[11] Patent Number: 5,966,746
[45] Date of Patent: Oct. 19, 1999

[54] SAFETY GOGGLES WITH ACTIVE VENTILATION SYSTEM

[75] Inventors: Mark G. Reedy, Omaha, Nebr.; Kevin L. Barton, Crescent, Iowa

[73] Assignee: Board of Regents of University of Nebraska, Lincoln, Nebr.

[21] Appl. No.: 09/008,419

[22] Filed: Jan. 16, 1998

[51] Int. Cl.⁶ .................................................. A61F 9/02
[52] U.S. Cl. ................................................. 2/436; 2/171.3
[58] Field of Search .............................. 2/436, 437, 435, 2/171.3, 8

[56] References Cited

U.S. PATENT DOCUMENTS

| | | |
|---|---|---|
| 3,031,675 | 5/1962 | Dubach ........................................ 2/437 |
| 3,368,220 | 2/1968 | Wenzel ............................................ 2/8 |
| 3,825,953 | 7/1974 | Hunter . | |
| 4,150,443 | 4/1979 | McNeilly . | |
| 4,443,893 | 4/1984 | Yamamoto . | |
| 4,890,335 | 1/1990 | Crowson ................................. 2/171.3 X |
| 4,996,981 | 3/1991 | Elenewski et al. . | |
| 5,099,525 | 3/1992 | Millauro . | |
| 5,372,130 | 12/1994 | Stern et al. . | |
| 5,452,480 | 9/1995 | Ryden . | |
| 5,592,936 | 1/1997 | Thomas, Jr. et al. . | |

*Primary Examiner*—Peter Nerbun
*Attorney, Agent, or Firm*—Shook, Hardy & Bacon LLP

[57] ABSTRACT

A goggles apparatus 10 is provided with an active ventilation system for reducing fogging of the goggles during use. The goggles apparatus includes, among other features, a lens 12, a body 14 supporting the lens and presenting shielding walls that define an interior space adjacent an interior surface of the lens, and inlet and outlet ports formed in the body. A fan 54 is supported in the outlet port of the goggles for drawing air through the inlet port into the interior space, and an air filter 32 is supported in the inlet port for treating air entering the goggles to protect against irritants reaching the eyes of the wearer.

15 Claims, 2 Drawing Sheets

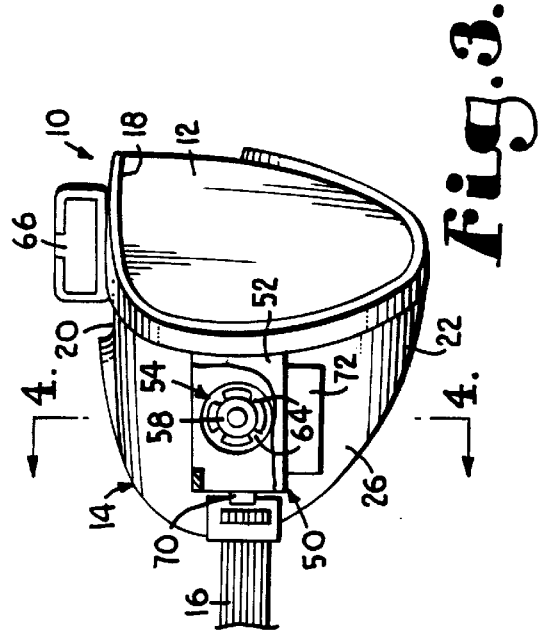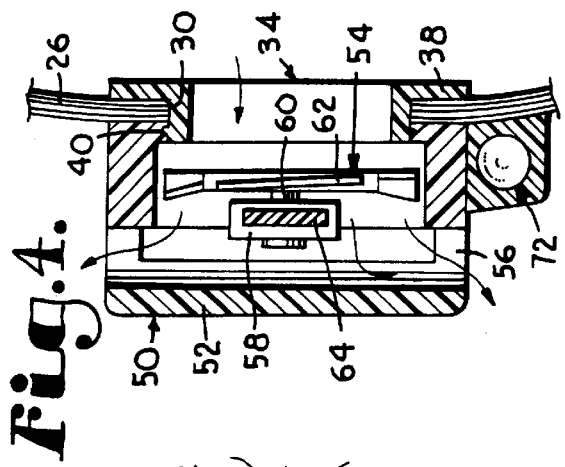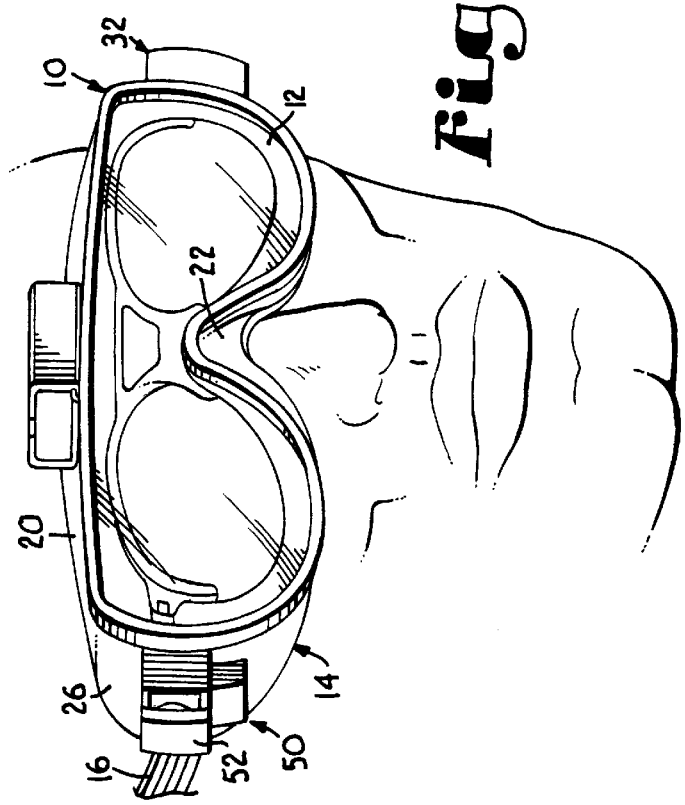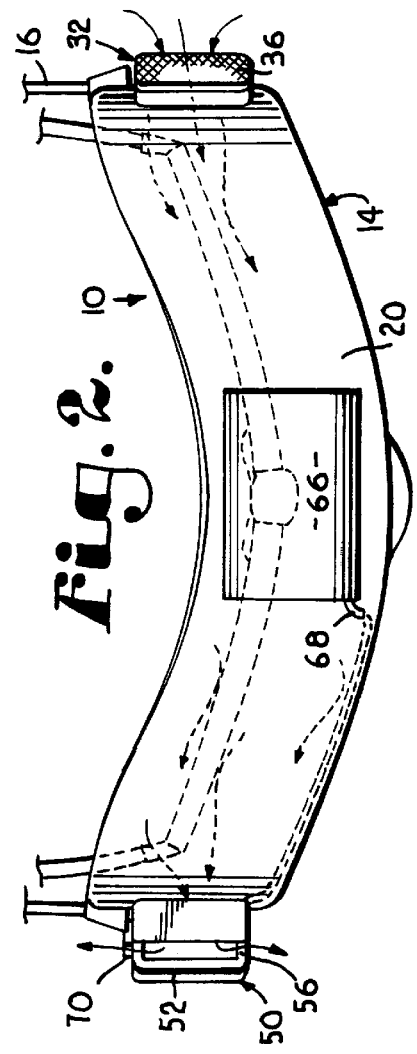

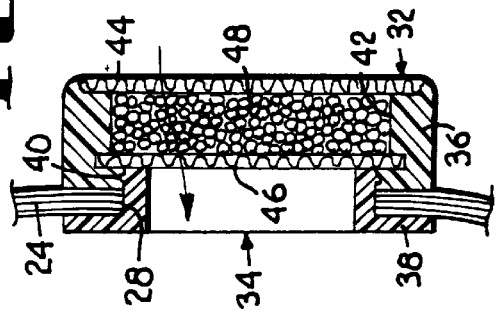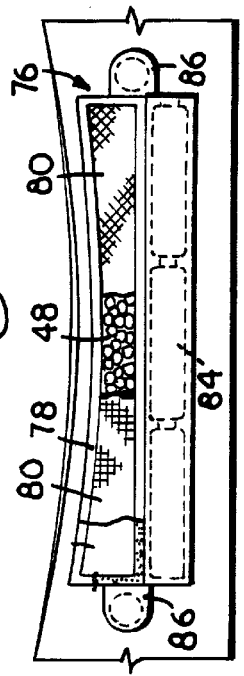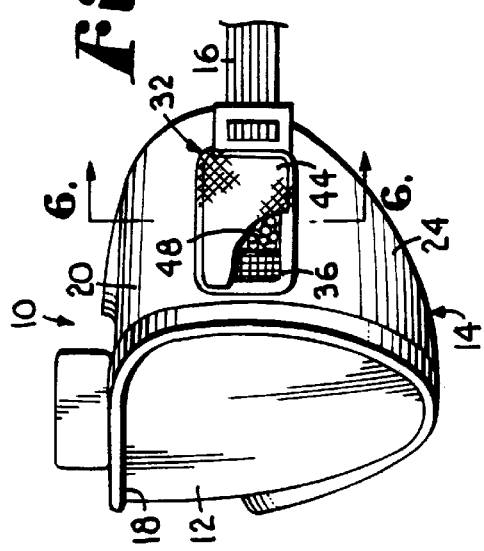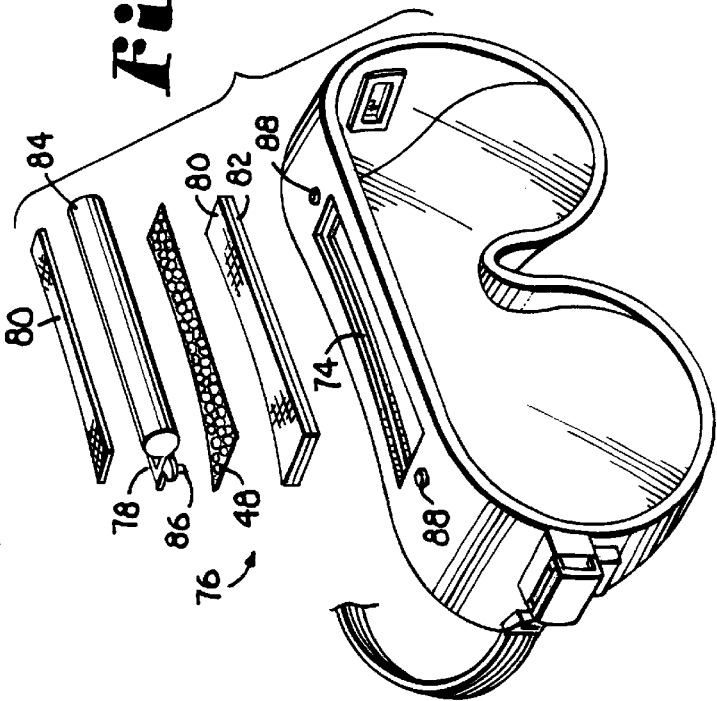

SAFETY GOGGLES WITH ACTIVE VENTILATION SYSTEM

CROSS-REFERENCE TO RELATED APPLICATIONS

"Not Applicable"

STATEMENT REGARDING FEDERALLY SPONSORED RESEARCH OR DEVELOPMENT

"Not Applicable"

BACKGROUND OF THE INVENTION

The present invention relates generally to safety goggles, and more particularly to a safety goggles apparatus having an active ventilation system for preventing fogging of the goggles during use.

The use of safety goggles for protecting the eyes of wearers from contact with wind, debris, chemicals and other foreign objects and irritants is widely known. Goggles have long been used by skiers, laboratory workers, and machine operators, but have gained recent acceptance in many other fields such as with health professionals, construction workers, landscape maintenance workers and others who work in environments where the air carries contaminants or debris that may irritate or cause damage to the workers' eyes if left unprotected. As such, safety goggles have many applications.

Although goggles provide protection to the wearers' eyes, they also present certain problems that are bothersome or problematic to the wearer, depending on the environment in which the worker is employed. One such problem is fogging of the wearer's eyeglasses within the goggles, or of the lens of the goggles, which occurs when warm, moist air within the goggles contacts a relatively cool lens. In many environments, such fogging is unacceptable and dangerous. For example, a laboratory worker handling dangerous chemicals during a reaction must be able to see what he or she is doing, and to monitor the progress of the reaction. There is often little room for error, and perfect vision is essential to the success of the procedure.

It is known to provide a goggles apparatus with an active ventilation system for moving air through the interior of the goggles to keep the lens from fogging. For example, it is known from U.S. Pat. No. 5,452,480, to Ryden, to provide a ski goggles construction including a plurality of ventilation openings in the body of the goggles, and a fan in communication with the interior space of the goggles for drawing air into the openings and through the interior space. Goggles of this general type work well in applications such as skiing where the ambient air being drawn into the goggles is fresh and free of irritants or the like. However, in environments where such debris is present in the ambient air, conventional constructions have a tendency to allow the debris to be drawn into the goggles, raising the risk of injury to the wearer.

BRIEF SUMMARY OF THE INVENTION

It is an object of the present invention to provide a goggles apparatus that provides all of the benefits of an active ventilation system while overcoming the problems encountered in the use of conventional goggles having such systems.

In accordance with this and other objects evident from the following description of a preferred embodiment of the invention, a goggles apparatus is provided which includes, among other features, a lens, a body supporting the lens and surrounding the wearer's eyes, an air treatment material supported in an inlet port of the body for treating air that passes through the inlet port into the interior space of the goggles, and a fan supported in an outlet port of the body for drawing air through the air treatment material into the interior space.

By providing a goggles apparatus in accordance with the present invention, numerous advantages are realized. For example, by providing a fan in the outlet port of the goggles body, an active ventilation system results, wherein ambient air can be continuously drawn into the interior space of the goggles to replace the air already within the space that has been exposed to the heat and humidity given off by the wearer. This airflow keeps the air temperature and humidity of the air within the interior space of the goggles equalized with ambient conditions so that fogging of the wearer's eyeglasses and of the lens of the goggles is minimized or eliminated. In addition, by placing an air treatment material in the inlet port of the goggles body, air entering the interior space is filtered, neutralized, or otherwise treated to remove irritants or debris that might otherwise get into the eyes of the wearer and cause discomfort or injury.

BRIEF DESCRIPTION OF THE SEVERAL VIEWS OF THE DRAWING

The preferred embodiment of the present invention is described in detail below with reference to the attached drawing, wherein:

FIG. 1 is a perspective view of a goggles apparatus constructed in accordance with the preferred embodiment of the present invention, illustrating the apparatus in a use position on the face of a wearer;

FIG. 2 is a fragmentary top plan view of the apparatus;

FIG. 3 is a fragmentary right side elevational view of the apparatus, partially broken away to illustrate a fan assembly forming a part thereof;

FIG. 4 is a sectional view taken along line 4—4 of FIG. 3, illustrating details of the fan assembly;

FIG. 5 is a fragmentary left side elevational view of the apparatus, partially broken away to illustrate a filter forming a part thereof;

FIG. 6 is a sectional view taken along line 6—6 of FIG. 5, illustrating details of the filter;

FIG. 7 is a fragmentary exploded perspective view of a goggles apparatus constructed in accordance with an alternate preferred embodiment of the present invention; and FIG. 8 is a fragmentary top plan view of a filter assembly forming a part of the alternate preferred embodiment of the apparatus.

DETAILED DESCRIPTION OF THE INVENTION

A goggles apparatus 10 constructed in accordance with the preferred embodiment of the invention is shown in FIG. 1, and generally includes a lens 12, a flexible body 14 supporting the lens and presenting a rear edge shaped to conform to the face of a wearer, and a strap 16 for holding the goggles in place over the eyes of the wearer to protect against injury. The goggles are sized to accommodate the wearer's eyeglasses so that the goggles can be moved between a storage position on the forehead of the wearer to a use position over the wearer's eyes without the wearer having to remove his or her glasses.

The lens 12 is preferably formed of a transparent, high impact synthetic resin of known composition, and presents opposing interior and exterior lens surfaces that are preferably parallel to one another. Of course, prescription lenses having surfaces that are convex or concave relative to one another may also be employed. Likewise, in place of the single lens shown, a pair of side-by-side lenses may used, or plural stacked lenses or laminates that are arranged one on top of another. It is understood that the construction of the lens is not critical to the invention, and that any known lens material or configuration may be employed in the preferred embodiment without departing from the scope of the invention.

The goggles body is formed of any suitable material or materials, and functions to support the lens in position over the eyes and eyeglasses of the wearer. For example, a relatively pliant, flexible synthetic resin material such as that used in constructing the goggles bodies of conventional constructions is suitable. As with the lens, the particular body material or shape is not critical to the invention, and any known configuration of a goggles body can be employed in carrying out the preferred embodiment.

Turning to FIG. 3, the goggles body is generally tubular, presenting an opening 18 at one end within which the lens is supported, and an opening at the opposite end that is shaped to conform to the face of a wearer. The lens support opening 18 preferably includes structure for receiving and supporting the lens without allowing the lens to be forced inward into the face or eyes of the wearer. For example, a groove can be provided within which the lens is received, and a flange formed in the body around the circumference of the lens just inside of the groove. The flange thus acts to prohibit inward movement of the lens toward the face of the wearer. The opposite opening in the goggles body is shaped to present a curved upper edge segment adapted to engage the forehead of the wearer, arcuate side edge segments that wrap around the side of the wearer's face, and a w-shaped lower edge segment that lays against the cheeks of the wearer and across the wearer's nose.

Between the openings in the body are defined top, bottom and side walls 20, 22, 24 and 26 that define an interior space adjacent the interior surface of the lens between the lens and the wearer's face, the walls shield the eyes of the wearer from debris and other air-carried materials that might otherwise injure the wearer if the goggles were not in place. In the embodiment illustrated in FIGS. 1–6, the side walls 24, 26 of the body, shown in FIGS. 3 and 5, are each provided with a port, one of which functions as an inlet port 28, shown in FIG. 6, and the other an outlet port 30, shown in FIG. 4. In addition, as shown in FIG. 2, strap loops are formed in the body adjacent the side edge segments for supporting the strap 16 in such a way that the length of the strap can be adjusted to fit the head of any particular wearer.

With reference to FIG. 6, an air filter 32 or other air treatment device is supported in the inlet port of the goggles body, and generally includes a rectangular support element 34 received on the inside of the body 14 and a canister 36 supported on the outside of the body over the inlet port. The support element 34 is formed of rigid synthetic resin or the like, and includes a tubular body presenting a ring-shaped flange 38 at one end and a circumferentially extending, outwardly directed ridge 40 adjacent the opposite end. The flange 38 includes an outer diameter greater than the diameter of the inlet port 28 so that the flange holds the element in place within the inlet port. The ridge 40 is spaced from the flange by a distance slightly greater than the thickness of the goggles body at the inlet port so that the support element and ridge protrude from the goggles body a short distance.

The canister 36 is also tubular in shape, presenting a first end having an inner diameter equal to the outer diameter of the body of the support element, and an open second end. A circumferential groove is formed in the inside surface of the canister adjacent the first end, and is sized for receipt of the ridge 40 of the support element 34 so that the canister is secured in place on the support element over the inlet port when the ridge and groove engage one another. Preferably, the fit between the ridge and groove is such as to permit replacement of the canister once the air treatment material therein is spent. However, it is also possible to provide a more permanent connection of the canister, if desired.

The interior surface of the canister is stepped, presenting the first end that is received on the support element, an intermediate section 42 having a diameter greater than the first end, and the second end having a diameter larger still than the intermediate section for receiving a first screen 44. In addition, a circumferential groove is formed in the inside surface of the canister between the first end and the intermediate section 42 for receiving a second screen 46.

The first and second screens are spaced from one another by the length of the intermediate section of the canister, and define an interior space that is sized for receipt of any suitable air treatment material 48. Preferably, a filter or neutralizing material is employed. However, it is understood that any material can be used in the canister which treats air in some desirable fashion as the air enters the interior space of the goggles. Exemplary materials include sorptive materials such as alumina, zeolite, and carbon molecular sieves, activated charcoal, spun polymers, silica gel and the like. Suitable neutralizing materials include sodium bicarbonate, calcium gluconate, and other known neutralizing media. Likewise a conventional mesh filter material or HEPA filter can be employed.

Turning to FIG. 4, a fan assembly 50 is supported in the outlet port 30 of the goggles body, and generally includes a rectangular support element 34 received on the inside of the body, a shroud 52 supported on the outside of the body over the outlet port and a fan 54 for drawing air from the interior space of the goggles. The support element 34 is preferably identical to the element used to secure the filter in place in the inlet opening, and the parts of both elements are thus numbered the same.

The shroud 52 is preferably formed of a rigid synthetic resin or the like, and includes a first end having an inner diameter equal to the outer diameter of the body of the support element, and a closed second end. A circumferential groove is formed in the inside surface of the shroud adjacent the first end, and is sized for receipt of the ridge 40 of the support element so that the shroud is secured in place on the support element over the outlet port when the ridge and groove engage one another. Preferably, the fit between the ridge and groove is such as to permit replacement or service of the fan and shroud, if necessary. However, it is also possible to provide a more permanent connection of the shroud, if desired.

A plurality of radially extending slots or openings 56 are formed in the shroud adjacent the second end thereof for allowing air to be exhausted from the shroud after the air is drawn from the interior space of the goggles. The fan 54 is supported within the shroud between the first end and the slots, and includes a motor 58 presenting a rotary output shaft 60, and a fan blade 62. The motor 58 is supported within the shroud by two or more radially extending arms or spokes 64 that engage both the motor and the interior surface of the shroud, as shown in FIG. 3, and the spokes permit air drawn from the goggles to pass out the slots 56 in the shroud. As shown in FIG. 4, the fan blade 62 is affixed to the output shaft 60 of the motor and rotates with the shaft to provide active ventilation of the goggles.

As shown in FIG. 2, a battery 66 or other suitable power source is supported on the goggles body at any convenient location, and is connected to the motor of the fan by electrical conductors, such as wires or the like. The battery can be of any suitable type, and any other power source can be substituted for the battery without departing from the scope of the present invention.

With reference to FIG. 3, the circuit defined by the motor 58, the battery 66, and the wires 68 also includes a first switch 70 mounted on the shroud for manual movement between "on" and "off" positions, and a conventional tilt switch 72 or the like that is mounted on the shroud and is automatically moved between "off" and "on" positions by tilting of the goggles between storage and use orientations. Preferably, the first switch 70 includes three positions, a first of which is the "off" position, a second of which is an "on" position enabling activation of the fan when the tilt switch is also in the "on" position, and a third of which is an "on" position that overrides the tilt switch to continuously activate the fan regardless of the orientation of the goggles.

During use, a wearer places the goggles on his or her face in the usual fashion, and moves the first switch 70 to the second position which enables activation of the fan when the tilt switch is also in the "on" position. Because the tilt switch is oriented to close the circuit in the use orientation of the goggles shown in FIG. 1, the fan is activated, drawing air from within the goggles and through the outlet port. As such, a negative pressure is developed in the interior space of the goggles, drawing air into the inlet port through the canister 36.

Turning to FIG. 2, as air enters the canister, it passes the air treatment material, allowing chemicals and debris in the air to be filtered or neutralized before entering the goggles. In this manner, the wearer is protected against irritation or injury that might otherwise result. In addition, the cross-flowing air prevents the wearer's eyeglasses and the goggles lens from fogging by replacing the warm humid air adjacent the wearer's face with fresh air.

If the goggles are lifted from the wearer's face and moved onto his or her forehead, the angle of the tilt switch 72, shown in FIG. 3, changes, opening the circuit and deactivating the fan. As such, the fan does not run continuously in the storage orientation, and power is conserved. Of course, if the first switch 70 is moved to the third position, the fan will remain activated even though the tilt switch tilts to the "off" position.

An alternate construction of the preferred embodiment is shown in FIGS. 7 and 8, and generally includes all of the elements of the first described construction. However, in the alternate construction, the filter and power source are combined in a single assembly to reduce the number of parts used to make up the apparatus, and to simplify replacement of the air treatment material and the battery.

In the alternate construction, as shown in FIG. 7, the goggles body is provided with an outlet port identical to the outlet opening in the first construction, and the fan assembly is as described above. However, the inlet port 74 is formed in the top wall rather than the side wall, and extends across the top of the lens. An air filter 76 or other air treatment device is supported in the stepped inlet port, and generally includes a rectangular body 78 presenting a central opening within which air treatment material is received. The material is retained in the opening of the body by screens 80 that are secured to the filter body by an adhesive or the like, and the thickness of the body dictates the amount of air treatment material that can be employed. A gasket 82 may also be attached to the body, or to one of the screens, and substantially seals the perimeter of the body against the goggles when the filter is in place to prevent air from entering the goggles without passing through the air treatment material.

An elongated cylindrical sleeve 84 is secured to or formed along one side of the body, and is sized for receipt of one or more conventional batteries. Electrical conductors are coupled to the batteries within the sleeve, and a pair of snap-type electrical contacts or other suitable interconnectors are attached to the body for connecting the batteries electrically with sockets 88 that are connected by wires to the fan. The snap-type contacts may also provide physical retention of the body on the goggles to hold the filter in place, or the body can be supported on the goggles by flanges of the goggles body in a fashion similar to that used to mount the lens on the body. As such, the entire filter, including the battery, can be removed as a unit from the goggles to permit replacement thereof.

Although the invention has been described with reference to the preferred embodiment illustrated in the attached drawing figures, it is noted that substitutions may be made and equivalents employed herein without departing from the scope of the invention as recited in the claims.

We claim:

1. A goggles apparatus comprising:
   at least one lens presenting exterior and interior surfaces;
   a body supporting the lens and presenting shielding top, bottom, and two laterally spaced side walls that define an interior space adjacent the interior surface of the lens;
   inlet and outlet ports formed in the body;
   an air treatment material supported in the inlet port for treating air that passes through the inlet port into the interior space of the goggles;
   a fan supported in the outlet port for drawing air through the air treatment material into the interior space;
   a power source for powering the fan; and
   a circuit connecting the power source with the fan, wherein at least one inlet port is formed in one of the side walls and the outlet port is formed in the other of the side walls.

2. A goggles apparatus as recited in claim 1, wherein the inlet port is formed in the top wall of the body.

3. A goggles apparatus as recited in claim 1, wherein two laterally spaced side walls are presented by the body and the outlet port is formed in one of the side walls.

4. A goggles apparatus as recited in claim 1, wherein the air treatment material is selected from the group consisting of alumina, zeolite, carbon, activated charcoal, spun polymers, silica gel, sodium bicarbonate, and calcium gluconate.

5. A goggles apparatus as recited in claim 1, wherein the power source is a battery.

6. A goggles apparatus as recited in claim 1, wherein the circuit includes a switch for closing and opening the circuit to turn the fan on and off, the switch being moved between an "off" position and an "on" position by tilting of the goggles between a storage orientation and a use orientation.

7. A goggles apparatus as recited in claim 1, wherein the circuit includes a first switch for closing and opening the circuit to turn the fan on and off, the first switch being a manually operated switch moveable between "on" and "off" positions.

8. A goggles apparatus as recited in claim 7, wherein the circuit includes a second switch that is moved between an off position and an on position by tilting of the goggles between a storage orientation and a use orientation, the second switch being operable to activate the fan when the first switch is in the "on" position.

9. A goggles apparatus comprising:
   at least one lens presenting exterior and interior surfaces;
   a body supporting the lens and presenting shielding top, bottom, and side walls that define an interior space adjacent the interior surface of the lens;
   inlet and outlet ports formed in the body;
   an air treatment material supported in the inlet port for treating air that passes through the inlet port into the interior space of the goggles;
   a fan supported in the outlet port for drawing air through the air treatment material into the interior space;
   power source for powering the fan; and
   a circuit connecting the power source with the fan; and
   a canister for supporting the air treatment material in the inlet opening, the canister including a closed side wall presenting opposed open ends, a screen closing off each open end to retain the air treatment material within the canister, and at least one support element for supporting the canister on the body of the goggles over the inlet opening so that air enters the inlet opening through the canister.

10. A goggles apparatus as recited in claim 9, wherein the canister is removable from the goggles apparatus for replacement.

11. A goggles apparatus as recited in claim 9, wherein the power source is supported on the canister.

12. A goggles apparatus as recited in claim 11, wherein two support elements are provided for supporting the canister on the goggles, the two support elements including electrical contacts for connecting the power source to the circuit.

13. A goggles apparatus as recited in claim 12, wherein the support elements are snap-type electrical contacts.

14. A goggles apparatus as recited in claim 1, wherein the top, bottom and side walls of the body present a rear edge that is shaped for receipt against the face of a wearer in a use position of the goggles, the interior space being sized to accommodate a pair or eyeglasses on the wearer's face in the use position.

15. A goggles apparatus as recited in claim 1, wherein the air treatment material is a mesh filter.

* * * * *